United States Patent [19]

Kurono et al.

[11] Patent Number: 4,987,150

[45] Date of Patent: Jan. 22, 1991

[54] AGENT FOR INHIBITING BINDING OF 5-DIHYDRO-TESTOSTERONE WITH ANDROGEN RECEPTOR AS WELL AS PROCESS FOR OBTAINING SAME

[75] Inventors: Masayasu Kurono, Mie; Hidehumi Yamakawa, Kasugai; Takuya Koshizaka, Kasugai; Takehiko Suzuki, Kasugai; Eiichi Kato, Nagoya; Takafumi Iida, Kasugai; Nobuko Ohishi, Gifu; Kunio Yagi, Nagoya, all of Japan

[73] Assignee: Kabushiki Kaisha Vitamin Kenkyusho, Gifu, Japan

[21] Appl. No.: 210,489

[22] Filed: Jun. 23, 1988

[30] Foreign Application Priority Data

| Jun. 26, 1987 | [JP] | Japan | 62-157605 |
| Jul. 8, 1987 | [JP] | Japan | 62-168809 |
| Dec. 8, 1987 | [JP] | Japan | 62-308610 |
| Dec. 5, 1988 | [JP] | Japan | 63-113498 |

[51] Int. Cl.$^5$ ............................................. A61K 31/35
[52] U.S. Cl. .................................................... 514/455
[58] Field of Search ............... 514/455; 424/195.1, 424/74; 549/388, 392, 393

[56] References Cited

U.S. PATENT DOCUMENTS 3,133,864 5/1964 Hagiwara .............................. 424/74

FOREIGN PATENT DOCUMENTS

| 46-27558 | 8/1971 | Japan | 549/389 |
| 46-40342 | 11/1971 | Japan | 424/195.1 |
| 70605 | 4/1984 | Japan | 424/74 |
| 60-146826 | 2/1985 | Japan . | |
| 60-126218 | 5/1985 | Japan . | |
| 146829 | 8/1985 | Japan | 424/74 |
| 174706 | 9/1985 | Japan | 424/74 |

OTHER PUBLICATIONS

Komatsu et al., "Studies on the Constituents of *Swertia japonica*. IV. Isolation and Structure of Xanthones", *Chem. Pharm. Bull.*, 17(1) 155–162 (1969).

Ghosal et al., "Chemical Constituents of the Gentianaceae V: Tetraoxygenated Xanthones of *Swertia chirata* Buch.-Ham." *J. Pharm. Sci.*, 62(6) 926–930 (1973).

Conn's Current Therapy, 1984, pp. 599–603.
Current Therapy, 1981, p. 662.

*Primary Examiner*—John W. Rollins
*Attorney, Agent, or Firm*—Armstrong, Nikaido, Marmelstein, Kubovcik & Murray

[57] ABSTRACT

An agent for inhibiting the binding of 5α-dihydrotestosterone with androgen receptor, which comprises at least one extract from herbs or one of specific xanthone compounds, and a process for obtaining the agent.

2 Claims, No Drawings

AGENT FOR INHIBITING BINDING OF 5-DIHYDRO-TESTOSTERONE WITH ANDROGEN RECEPTOR AS WELL AS PROCESS FOR OBTAINING SAME

BACKGROUND OF THE INVENTION

1. Field of the Invention

The present invention relates to an anti-androgenic agent, and more particularly to an agent for inhibiting the binding of 5α-dihydrotestosterone (hereinafter referred to as "5α-DHT") with androgen receptor, and a process for obtaining the same.

2. Related Arts

Anti-androgenic medicines have been administered for preventing or curing androgen dependent diseases, for instance, hypertrichosis, acne, male pattern alopecia, prostatomegaly, prostatic tumor, male precocity and the like. In general, the medicines comprise a compound having a steroid skeleton as an effective ingredient, and thus the administration thereof has been limited in dose to prevent side effects.

Referring now to the activity of an anti-androgenic substance, anti-androgenic action means an action for decreasing the androgenic activity of testosterone, and is caused by an inhibition of binding of 5α-DHT with androgen receptor, or inhibition of the 5α-reductase activity which reduces testosterone into 5α-DHT.

Recently, it has been reported in Jap. Pat. No. 60-146829 (A) that an extract obtained from various herbs shows the latter anti-androgenic action, namely a certain inhibition of the activity of 5α-reductase. The present inventors have also found that an extract of Swertia japonica Makino shows such inhibition and that the compound showing the inhibition is oleanolic acid as one of oleanane type triterpene compounds, and reported the same in Jap. Pat. No. 60-126218 (A). Among said two anti-androgenic actions, it has been considered that the former action, namely, the inhibition of binding of 5 α-DHT with androgen receptor is more effective than the latter, but there is no report whether an extract of herbs shows such inhibition of binding or not.

SUMMARY OF THE INVENTION

The basic object the invention lies in screening and investigation of various herb extracts to find those showing inhibition of binding of 5α-DHT with androgen receptor to provide effective anti-androgenic agents.

The principal object of the invention is to provide a process for effective extraction of substances which inhibit this binding.

An additional but important object of the invention is to identify substances, so as to make their syntheses possible.

In order to attain the objects, the present inventors have obtained extracts from various herbs and studied on their pharmacological actions to find those extracts of certain herbs that show the desired action of binding-inhibition, and finally established the invention.

According to the invention, the basic object is attained by an agent for inhibiting the binding of 5α-DHT with androgen receptor, which comprises, as an effective ingredient, at least one extract obtained from the following list of herbs: Swertia japonica Makino, Swertia pseudochinensis Hara, Swertia tosaensis Makino, Swertia randaiensis Hayata, Swertia chirata Buch. -Ham., Sasa paniculata Makino et Shibata var. albo-marginata Makino, Scutellariae Radix (Scutellaria Root), Glycyrrhizae Radix (Glycyrrhiza), Rhei Rhizoma (Rhubarb), Panacis Japonici Rhizoma (Panax Rhizome), Aurantii Nobilis Pericarpium (Citrus Unshiu Peel), Arecae Semen (Areca), Caryophylli Flos (Clove), Bupleuri Radix (Bupleurum Root), Coicis Semen (Coix Seed), Cnidii Rhizoma (Cnidium Rhizome), Paeoniae Radix (Peony Root), Gambir (Gambir), Angelicae Radix (Japanese Angelica Root), Polygalae Radix (Polygala Root), Plantaginis Semen (Plantago Seed), Prunellae Spica (Prunella Spike), Picrasmae Lignum (Picrasma Wood), Foeniculi Fructus (Fennel), Geranii Herba (Geranium Herb), Catalpae Fructus (Catalpa Fruit), Perillae Herba (Perilla Herb), Schizonepetae Spica (Schizonepeta Spike), Valerianae Radix (Japanese Valerian), Pharbitidis Semen (Pharbitis Seed), Bufonis Venenum (Toad Venom), Rosae Fructus (Rose Fruit), and Resina Pini (Rosin).

The principal object of the invention can be attained by a process for obtaining an agent inhibiting the binding of 5α-DHT with androgen receptor, which comprises a step of extracting at least one of said herbs. As the solvent, pentane, hexane, heptane, cyclohexane or the like fatty hydrocarbon; methylene chloride, chloroform, carbon tetrachloride or the like halogenated hydrocarbon; methanol, ethanol, isopropanol or the like alcohol; acetic acid, formic acid or the like acid solution; sodium hydroxide, potassium hydroxide or the like alkali solution; diethyl ether or the like ether; ethyl acetate or the like ester; acetone or the like ketone; water or a mixture thereof can be listed, but it is preferable to use the organic solvent in distilled water, in which mixture water occupies 10 to 50% by the volume. For instance, ethanol, isopropanol, or acetone in water is preferable, if Swertia japonica Makino, Swertia pseudochinensis Hara, Swertia tosaensis Makino, Swertia randaiensis Hayata, or Swertia chirata Buch. -Ham. is to be treated. Conditions for the extraction, namely, volume of the solvent, temperature, soaking time of period, and number of extractions depend on the kind of raw material (herb) and of solvent. For instance, with Swertia japonica Makino, it is preferable to use 70% (v/v) ethanol in distilled water in the volume of about 5 to 10 times (v/w) based on the weight of the dried herb, to soak it for 1 day to 1 week at room temperature, and to repeat this procedure twice. The resulting extract can be employed as it is, as an effective ingredient for medicines, or may be diluted or concentrated.

The additional object of the invention is attained by studying and investigating each of the extracts from the pharmaceutical view point.

The present inventors have found that the extracts contain 1,3, 5,8-tetrahydroxyxanthone which shows the inhibition of binding of 5α-DHT with androgen receptor. Extracts of the following herbs contain this compound: Swertia japonica Makino, Swertia pseudochinensis Hara, Swertia tosaensis Makino, Swertia randaiensis Hayata, Swertia chirata Buch. -Ham., and the like. Based on this finding, the present inventors have chemically synthesized the following compounds analogous to said 1,3,5,8-tetrahydroxyxanthone and checked their pharmacological activity to find which show inhibition of the binding-activity in question.

1,3,6,8-Tetrahydroxyxanthone; 1,4,6-trihydroxyxanthone; 1,3,5-trihydroxyxanthone; 1,3,6-trihydroxyxanthone; 1,3,8-trihydroxyxanthone; 1,3-dihydroxyxanthone; and 1,6-dihydroxyxanthone.

Said xanthone compounds are well-known, but pharmaceutical activity, particularly anti-androgenic activity thereof has not been known.

The xanthone compounds can be extracted from the herbs by already published procedures, for instance, by the method as disclosed in "Yakugaku Zasshi (translated as-Journal of the Pharmaceutical Society of Japan)" Vol. 89, pages 410–417 (1969) and isolated through a suitable purification procedure, for instance, distribution between water and a solvent, column chromatography, thin layer chromatoraphy, high performance liquid chromatography or the like. As a solvent for the extraction and purification, those as referred to may be employed. Further, each of the xanthone compounds has a simple structure and thus can be chemically synthesized in a routine manner. One of the xanthone compounds, namely 1,3,6-trihydroxyxanthone can also be prepared with resorcinol and 2,4,6-trihydroxybenzoic acid, in accordance with the method as disclosed in "J. Chem. Soc." pages 3982–3985 (1955).

In the case of preparing an anti-androgenic medicine with the agent according to the invention, namely at least one of the extracts and xanthone compounds either in the form of a tablet, capsule, powder, granule, solution for oral administration, lotion, liniment, cream, ointment, or suppository is applicable as the medicine. In connection with this, the medicine can be prepared in the conventional manner. An amount of the extract or compound for administration to human depends on conditions of illness, age of patient, form of the medicine, and other factors, but in general, for an adult, 0.002–300 mg/day for oral administration and 0.005–600 mg/day at one time or divided into 2 to 4 times in the case of the suppository are preferable. In the case of topical treatment, it is preferable to prepare the medicine containing the effective ingredient in an amount of 0.00001–45% by weight and to administer it in several times/day, in accordance with the conditions of illness.

DETAILED DESCRIPTION OF THE PREFERRED EMBODIMENTS

The invention will now be further explained in detail with reference to Extract Preparation Examples, Pharmacological Test Example, Reference Examples, Test Examples, and Medicine Preparation Examples.

EXAMPLES 1–9

Each of 960 g of finely cut dried *Swertia japonica* Makino, 10 g of finely cut dried *Swertia pseudochinesis* Hara, 15 of finely cut dried Scutellariae Radix, 15 of finely cut dried Glycyrrhizae Radix, 15 g of finely cut dried Rhei Rhizoma, 7.52 g of finely cut dried Panacis Japonici Rhizoma, 15 g of *Sasa paniculata* Makino et Shibata var. *albo-marginata* Makino, 15 g of finely cut dried Aurantii Nobilis Pericarpium, or 15 g of finely cut dried Arecae Semen was soaked in 70% (v/v) ethanol is distilled water in a volume of 10 times (v/w) based on the weight of the dried herb for 1 to 6 days, and then filtered to obtain a primary extract. To each residue, ethanol solution having the concentration as above and a volume of 5 times (v/w) based on the weight of the herb was added to repeat the treatment as above to obtain a secondary extract. The primary and secondary extracts were combined and dried in vacuo to obtain the following extracts.

| | | |
|---|---|---|
| (1) Extract of *Swertia japonica* Makino | 275 (g) |
| (2) Extract of *Swertia pseudochinensis* Hara | 2.77 |
| (3) Extract of *Scutellariae Radix* | 5.47 |
| (4) Extract of *Glycyrrhizae Radix* | 2.90 |
| (5) Extract of *Rhei Rhizoma* | 5.51 |
| (6) Extract of *Panacis Japonici Rhizoma* | 3.29 |
| (7) Extract of *Sasa paniculata* Makino et Shibata var. *albo-marginata* Makino | 2.11 |
| (8) Extract of *Aurantii Nobilis Pericarpium* | 6.24 |
| (9) Extract of *Arecae Semen* | 1.23 |

PHARMACOLOGICAL TEST EXAMPLE 1

This test was carried out in accordance with the method as disclosed in "J. Steroid Biochem." Vol. 19, pages 1141–1146 (1983).

(a) Preparation of androgen receptor

From a male Syrian hamster 16 hours after castration, a sebaceous gland in flank organ was excised and homogenized in 5–10 times (volume) of 50 mM-Tris-HCl buffer (pH 7.4) containing 1.5 mM-EDTA, 1 mM-DTT, 10 mM-Na$_2$MoO$_4$, and 10% (w/v) glycerol. The homogenate was centrifuged at 3,000 rpm and 0°–4° C. for 10 minutes to obtain the supernatant, which was further centrifuged at 30,000 rpm and 0°–4° C. for 1 hour to obtain the supernatant to be employed as androgen receptor.

(b) Determination of inhibitory activity

A mixture (150 μl) of 1 nM [$^3$H]R1881 (methyltrienolone, 86.0 Ci/mmol), 1μM triamcinolone acetonide, the androgen receptor in said Item a, and the test sample (each of the extracts in said Examples 1 to 9 of various concentrations) was incubated at 0° C. for 16 hours. Then the mixture was added with a suspension (500 μl) of 0.5% charcoal and 0.05% dextran T-70. After standing at 0° C. for 10 minutes, the mixture was centrifuged at 3,000 rpm for 10 minutes. The supernatent (300 μl) was mixed with a liquid scintillator to measure the radioactivity due to binding of [$^3$H]R1881 with the androgen receptor in scintillation counter. The inhibition rate of each extract was calculated according to the following equation.

$$\text{Inhibition } (\%) = [(c-s)/c] \times 100$$

wherein
  c: specific binding amount of [$^3$H]R1881 with androgen receptor without addition of test sample; and
  s: specific binding amount of [$^3$H]R1881 with androgen receptor with addition of the test sample.
(c) Results
Resluts are shown in following Table 1.

TABLE 1

| Test sample | Concentration (μg/ml) | Inhibition (%) |
|---|---|---|
| Example 1 | 510 | 12.2 |
| 2 | 1230 | 28.0 |
| 3 | 320 | 51.8 |
| 4 | 860 | 40.4 |
| 5 | 330 | 47.6 |
| 6 | 1940 | 18.8 |
| 7 | 3100 | 26.4 |
| 8 | 9200 | 18.8 |
| 9 | 1820 | 58.0 |

EXAMPLE 10

5 g of finely cut dried *Swertia japonica* Makino or coarse pieces thereof were soaked in 50 ml of 90% (v/v)

ethanol in distilled water for 24 hours at room temperature, and then filtered to obtain a primary extract. To the residue, 25 ml of ethanol solution having said concentration were added to repeat the treatment as above to obtain a secondary extract. The extracts were combined and ethanol solution having said concentration was added thereto to make its volume to be 75 ml.

EXAMPLE 11

5 g of finely cut dried *Swertia japonica* Makino or coarse pieces thereof were soaked in 50 ml of 70% (v/v) ethanol in distilled water for 24 hours at room temperature, and then filtered to obtain a primary extract. To the residue, 25 ml of ethanol solution having said concentration were added to repeat the treatment as above to obtain a secondary extract. The extracts were combined and ethanol solution having said concentration was added thereto to make its volume to be 75 ml.

EXAMPLE 12

5 g of finely cut dried *Swertia japonica* Makino or coarse pieces thereof were soaked in 50 ml of 50% (v/v) ethanol in distilled water for 24 hours at room temperature, and then filtered to obtain a primary extract. To the residue, 25 ml of ethanol solution having said concentration were added to repeat the treatment as above to obtain a secondary extract. The extracts were combined and ethanol solution having said concentration was added thereto to make its volume to be 75 ml.

EXAMPLE 13

5 g of finely cut dried *Swertia japonica* Makino or coarse pieces thereof were soaked in 50 ml of 90% (v/v) isopropanol in distilled water for 24 hours at room temperature, and then filtered to obtain a primary extract. To the residue, 25 ml of isopropanol solution having said concentration were added to repeat the treatment as above to obtain a secondary extract. The extracts were combined and isopropanol solution having said concentration was added thereto to make its volume to be 75 ml.

EXAMPLE 14

5 g of finely cut dried *Swertia japonica* Makino or coarse pieces thereof were soaked in 50 ml of 70% (v/v) isopropanol in distilled water for 24 hours at room temperature, and then filtered to obtain a primary extract. To the residue, 25 ml of isopropanol solution having said concentration were added to repeat the treatment as above to obtain a secondary extract. The extracts were combined and isopropanol solution having said concentration was added thereto to make its volume to be 75 ml.

EXAMPLE 15

5 g of finely cut dried *Swertia japonica* Makino or coarse pieces thereof were soaked in 50 ml of 50% (v/v) isopropanol in distilled water for 24 hours at room temperature, and then filtered to obtain a primary extract. To the residue, 25 ml of isopropanol solution having said concentration were added to repeat the treatment as above to obtain a secondary extract. The extracts were combined and isopropanol solution having said concentration was added thereto to make its volume to be 75 ml.

EXAMPLE 16

5 g of finely cut dried *Swertia japonica* Makino or coarse pieces thereof were soaked in 50 ml of 90% (v/v) acetone in distilled water for 24 hours at room temperature, and then filtered to obtain a primary extract. To the residue, 25 ml of acetone solution having said concentration were added to repeat the treatment as above to obtain a secondary extract. The extracts were combined and acetone solution having said concentration was added thereto to make its volume to be 75 ml.

EXAMPLE 17

5 g of finely cut dried *Swertia japonica* Makino or coarse pieces thereof were soaked in 50 ml of 50% (v/v) acetone in distilled water for 24 hours at room temperature, and then filtered to obtain a primary extract. To the residue, 25 ml of acetone solution having said concentration were added to repeat the treatment as above to obtain a secondary extract. The extracts were combined and acetone solution having said concentration was added thereto to make its volume to be 75 ml.

REFERENCE EXAMPLE 1

5 g of finely cut dried *Swertia japonica* Makino or coarse pieces thereof were soaked in 50 ml of ethanol for 24 hours at room temperature, and then filtered to obtain a primary extract. To the residue, 25 ml of ethanol were added to repeat the treatment as above to obtain a secondary extract. The extracts were combined and ethanol was added thereto to make its volume to be 75 ml.

REFERENCE EXAMPLE 2

5 g of finely cut dried *Swertia japonica* Makino or coarse pieces thereof were soaked in 50 ml of 40% (v/v) ethanol in distilled water for 24 hours at room temperature, and then filtered to obtain a primary extract. To the residue, 25 ml of ethanol solution having said concentration were added to repeat the treatment as above to obtain a secondary extract. The extracts were combined and ethanol solution having said concentration was added thereto to make its volume to be 75 ml.

REFERENCE EXAMPLE 3

5 g of finely cut dried *Swertia japonica* Makino or coarse pieces thereof were soaked in 50 ml of isopropanol for 24 hours at room temperature, and then filtered to obtain a primary extract. To the residue, 25 ml of isopropanol were added to repeat the treatment as above to obtain a secondary extract. The extracts were combined and isopropanol was added thereto to make its volume to be 75 ml.

REFERENCE EXAMPLE 4

5 g of finely cut dried *Swertia japonica* Makino or coarse pieces thereof were soaked in 50 ml of 30% (v/v) isopropanol in distilled water for 24 hours at room temperature, and then filtered to obtain a primary extract. To the residue, 25 ml of isopropanol solution having said concentration were added to repeat the treatment as above to obtain a secondary extract. The extracts were combined and isopropanol solution having said concentration was added thereto to make its volume to be 75 ml.

REFERENCE EXAMPLE 5

5 g of finely cut dried *Swertia japonica* Makino or coarse pieces thereof were soaked in 50 ml of acetone for 24 hours at room temperature, and then filtered to obtain a primary extract. To the residue, 25 ml of acetone were added to repeat the treatment as above to obtain a secondary extract. The extracts were combined and acetone was added thereto to make its volume to be 75 ml.

REFERENCE EXAMPLE 6

5 g of finely cut dried *Swertia japonica* Makino or coarse pieces thereof were soaked in 50 ml of 40% (v/v) acetone in distilled water for 24 hours at room temperature, and then filtered to obtain a primary extract. To the residue, 25 ml of acetone solution having said concentration were added to repeat the treatment as above to obtain a secondary extract. The extracts were combined and acetone solution having said concentration was added thereto to make its volume to be 75 ml.

REFERENCE EXAMPLE 7

5 g of finely cut dried *Swetria japonica* Makino or coarse pieces thereof were soaked in 50 ml of 70% (v/v) methanol in distilled water for 24 hours at room temperature, and then filtered to obtain a primary extract. To the residue, 25 ml of methanol solution having said concentration were added to repeat the treatment as above to obtain a secondary extract. The extracts were combined and methanol solution having said concentration was added thereto to make its volume to be 75 ml.

REFERENCE EXAMPLE 8

5 g of finely cut dried *Swertia japonica* Makino or coarse pieces thereof were soaked in 50 ml of diethylether for 24 hours at room temperature, and then filtered to obtain a primary extract. To the residue, 25 ml of diethylether were added to repeat the treatment as above to obtain a secondary extract. The extracts were combined and diethylether was added thereto to make its volume to be 75 ml.

TEST EXAMPLE 1

Extract content, yield and desmethylbellidifolin content for each of the extracts obtained by said Examples 10 to 17 and Reference Examples 1 to 7 were measured. Results are shown in the following Table 2. Further, contents of extract and desmethylbellidifolin per 1 g of *Swertia japonica* Makino are also shown in the following Table 3. In each case, the content of desmethylbellidifolin was determined by high performance liquid chromatography carried out under the following conditions.

HPLC column: Silica gel ODS (4.6×250 mm).
Solvent:
A, 0.02M-KH$_2$PO$_4$:CH$_3$OH=1:1
B, CH$_3$OH
  0–10 min.;
    A, 100%
    B, 0%
  10→34 min.;
    A, 100%→20%
    B, 0%→80%
  34–45 min.;
    A, 20%
    B, 80%
Detector: UV (255 nm).
Flow rate: 1 ml/min.
Detection limit: 0.01 μg/ml.

TABLE 2

| | Extract from *Swertia japonica* Makino | | Desmethylbellidifolin (μg/ml) |
|---|---|---|---|
| | Content (mg/ml) | Yield (%) | |
| Example | | | |
| 10 | 24.0 | 36.0 | 17.6 |
| 11 | 20.9 | 31.4 | 24.1 |
| 12 | 24.0 | 36.0 | 25.7 |
| 13 | 17.4 | 26.1 | 26.1 |
| 14 | 21.6 | 32.4 | 25.4 |
| 15 | 19.7 | 29.6 | 16.6 |
| 16 | 20.1 | 30.2 | 36.2 |
| 17 | 21.9 | 32.9 | 26.2 |
| Reference Example | | | |
| 1 | 11.8 | 17.7 | 7.8 |
| 2 | 21.6 | 32.4 | 9.2 |
| 3 | 9.2 | 13.8 | 6.3 |
| 4 | 20.4 | 30.6 | 1.0 |
| 5 | 7.8 | 11.7 | 6.9 |
| 6 | 21.4 | 32.1 | 8.3 |
| 7 | 20.1 | 30.2 | 8.1 |
| 8 | 3.0 | 4.5 | 1.5 |

TABLE 3

| | Extract from *Swertia joponica* Makino (mg/g of dried herb) | Desmethylbellidifolin content (μg/g of dried herb) |
|---|---|---|
| Example | | |
| 10 | 360 | 264 |
| 11 | 314 | 362 |
| 12 | 360 | 386 |
| 13 | 261 | 392 |
| 14 | 324 | 381 |
| 15 | 296 | 249 |
| 16 | 302 | 543 |
| 17 | 329 | 393 |
| Reference Example | | |
| 1 | 177 | 117 |
| 2 | 324 | 138 |
| 3 | 138 | 95 |
| 4 | 306 | 15 |
| 5 | 117 | 104 |
| 6 | 321 | 125 |
| 7 | 302 | 122 |
| 8 | 45 | 23 |

TEST EXAMPLE 2

The inhibitory effect of the following test samples (xanthone compounds which were chemically synthesized) on androgen binding activity was measured in the manner as disclosed in Pharmacological Test Example 1 and a concentration for 50% inhibition was calculated based on the inhibition rate. Results are shown in the following Table 4.

TEST SAMPLES

A; 1,3,5,8-Tetrahydroxyxanthone
B; 1,3,6,8-Tetrahydroxyxanthone
C; 1,4,6-Trihydroxyxanthone
D; 1,3,5-Trihydroxyxanthone
E; 1,3,6-Trihydroxyxanthone
F; 1,3,8-Trihydroxyxanthone
G; 1,3-Dihydroxyxanthone
H; 1,6-Dihydroxyxanthone

TABLE 4

| Test sample | Concentration for 50% Inhibition (M) |
|---|---|
| A | $8.0 \times 10^{-6}$ |
| B | $5.1 \times 10^{-6}$ |
| C | $1.8 \times 10^{-6}$ |
| D | $3.4 \times 10^{-5}$ |
| E | $4.1 \times 10^{-6}$ |
| F | $2.0 \times 10^{-5}$ |
| G | $5.3 \times 10^{-5}$ |
| H | $7.6 \times 10^{-6}$ |

MEDICINE PREPARATION EXAMPLE 1

Liniment

Prescription:

| | |
|---|---|
| Extract of *Swertia japonica* Makino (Example 1) | 300 ml |
| Tragacanth | 50 g |
| Glycerin | 30 ml |
| Ethanol | 100 ml |
| Purified water | Remainder |
| Total | 1000 ml |

To ethanol in a mortar, the tragacanth was mixed. The mixture was added with the extract, glycerin and further with 500 ml of water to make a paste, which was then turned into a liniment by the addition of the remaining water.

MEDICINE PREPARATION EXAMPLE 2

Lotion

Prescription:

| | |
|---|---|
| Extract of *Swertia japonica* Makino (Example 1) | 45 ml |
| Hydroxypropylcellulose | 1 g |
| Macrogol 400 | 10 ml |
| Purified water | Remainder |
| Total | 100 ml |

To a mixture of the extract and macrogol 400, hydroxypropylcellulose was added. The mixture was filled up to 100 ml with water and treated with a vacuum homogenizer to prepare a lotion.

REFERENCE EXAMPLE 9

Composition for Preparation

The extract of *Swertia japonica* Makino obtained by Example 1 was concentrated until its volume was reduced to 1/25 of the original. To the concentrate, 10-fold amount (w/w) of dextrin was added and sufficiently mixed to prepare a composition, in which the extract was uniformly dispersed.

MEDICINE PREPARATION EXAMPLE 3

Cream or Ointment

Prescription:

| | |
|---|---|
| Composition (Reference Example 9) | 30 g |
| Diethyl sebacate | 8 g |
| Spermaceti | 5 g |
| Sodium polyoxyethyleneoleylether phosphate | 6 g |
| Sodium benzoate | 0.5 g |
| Vaseline | Remainder |
| Total | 100 g |

Cream or ointment was prepared in the conventional manner with the above ingredients.

MEDICINE PREPARATION EXAMPLE 4

Suppository

Prescription:

| | |
|---|---|
| Composition (Reference Example 9) | 60 mg |
| Fatty base (Cacao butter) | 1640 mg |
| | 1700 mg/piece |

To the cacao butter, the composition was mixed to disperse it, and and the mixture was molded into a suppository in the conventional manner.

MEDICINE PREPARATION EXAMPLE 5

Powder

Prescription:

| | |
|---|---|
| Composition (Reference Example 9) | 30 mg |
| Lactose | 800 mg |
| Corn starch | 170 mg |
| | 1000 mg/package |

Powder was prepared in the conventional manner with the above ingredients.

MEDICIENE PREPARATION EXAMPLE 6

Granule

Preparation:

| | |
|---|---|
| Composition (Reference Example 9) | 30 mg |
| Lactose | 754 mg |
| Corn starch | 200 mg |
| Hydroxypropylcellulose | 16 mg |
| | 1000 mg/package |

To a mixture of the composition, lactose and corn starch, an aqueous solution of hydroxypropylcellulose was mixed. The mixture was granulized in the conventional manner.

MEDICINE PREPARATION EXAMPLE 7

Tablet, coated tablet and sugar-coated tablet

Prescription:

| | |
|---|---|
| Composition (Reference Example 9) | 30 mg |
| Crystalline cellulose | 40 mg |
| Lactose | 52.5 mg |
| Corn starch | 30 mg |
| Magnesium stearate | 7.5 mg |
| | 160 mg/tablet |

The ingredients were mixed to prepare tablets in the conventional manner.

Some of the tablets were coated in the conventional manner with a water-soluble coating agent having the prescription given below. Some of the resulting coated tablets were further treated with subcoating agent and coloring agent in the conventional manner and having the following prescriptions, to prepare sugar-coated tablets, and these prescriptions are also given below.

Prescription for water-soluble coating agent:

| | |
|---|---|
| Hydroxypropylcellulose | 40 g |
| Macrogol 6000 | 10 g |
| Titanium oxide | 3 g |
| Talc | 5 g |
| Purified water | 942 g |

Prescription for subcoating agent:

| | |
|---|---|
| Sucrose | 40 g |
| Gelatin | 0.5 g |
| Acacia | 1.4 g |
| Precipitated calcium carbonate | 22 g |
| Talc | 15.6 g |
| Purified water | 20 g |

Prescription for coloring agent:

| | |
|---|---|
| Sucrose | 10 g |
| Titanium oxide | 73 g |
| Lake pigment | 56 g |
| Purified water | 5 g |

MEDICINE PREPARATION EXAMPLE 8

Capsule

Prescription:

| | |
|---|---|
| Composition (Reference Example 9) | 30 mg |
| Lactose | 104 mg |
| Corn starch | 40 mg |
| Hydroxypropylcellulose | 16 mg |
| | 190 mg/capsule |

To a mixture of the composition, lactose and corn starch, an aqueous solution of hydroxypropylcellulose was mixed. The mixture was granulized in a conventional manner. The granules were packed into hard gelatin capsules to prepare capsules.

MEDICINE PREPARATION EXAMPLE 9

Liniment

The desired liniment was prepared in the same manner as that in Medicine Preparation Example 1, except that an ethanol solution of 2.5 mg of 1,3,5,8-tetrahydroxyxanthone was employed in lieu of the extract.

MEDICINE PREPARATION EXAMPLE 10

Lotion

The desired lotion was prepared in the same manner as that in Medicine Preparation Example 2, except that an ethanol solution of 0.5 mg of 1,3,5,8-tetrahydroxyxanthone was employed in lieu of the extract.

REFERENCE EXAMPLE 10

Composition for Preparation 1,3,5,8-Tetrahydroxyxanthone was dissolved in a 100-fold excess (w/w) of ethanol and therewith, a 5-fold excess (w/w) of dextrin was mixed. The mixture was dried to prepare a desired composition, wherein the xanthone compound was uniformly dispersed.

The dextrin as the carrier may be changed to a starch, lactose, lighter silic acid anhydride, magnesium metasilic aluminate, or the like.

MEDICINE PREPARATION EXAMPLE 11

Cream or Ointment

The desired cream or ointment was prepared in the same manner as that in Medicine Preparation Example 3, except that the composition as described in Reference Example 10 was employed in lieu of that in Reference Example 9.

MEDICINE PREPARATION EXAMPLE 12

Suppository

The desired suppository was prepared in the same manner as that in Medicine Preparation Example 4, except that the composition as described in Reference Example 10 was employed in lieu of that in Reference Example 9.

MEDICINE PREPARATION EXAMPLE 13

Powder

The desired powder was prepared in the same manner as that in Medicine Preparation Example 5, except that the composition as described in Reference Example 10 was employed in lieu of that in Reference Example 9.

MEDICINE PREPARATION EXAMPLE 14

Granule

The desired granule was prepared in the same manner as that in Medicine Preparation Example 6, except that the composition as described in Reference Example 10 was employed in lieu of that in Reference Example 9.

MEDICINE PREPARATION EXAMPLE 15

Tablet, Coated Tablet and Sugar-coated Tablet

The desired tablet, coated tablet and sugar-coated tablet were prepared in the same manner as that in Medicine Preparation Example 7, except that the composition as described in Reference Example 10 was employed in lieu of that in Reference Example 9.

MEDICINE PREPARATION EXAMPLE 16

Capsule

The desired capsule was prepared in the same manner as that in Medicine Preparation Example 8, except that the composition as described in Reference Example 10 was employed in lieu of that in Reference Example 9.

What is claimed is:

1. An anti-androgenic composition which comprises an effective amount of at least one xanthone compound selected from the group consisting of 1,3,5,8-tetrahydroxyxanthone, 1,3,6,8-tetrahydroxyxanthone, 1,4,6-trihydroxyxanthone, 1,3,5-trihydroxyxanthone, 1,3,6-trihydroxyxanthone, 1,3,8-trihydroxyxanthone, 1,3-dihydroxyxanthone, and 1,6-dihydroxyxanthone, and a pharmaceutically acceptable carrier.

2. A method for an treatment of the androgen dependent diseases in mammals comprising administering an effective amount of at least one xanthone compound selected from the group consisting of 1,3,5,8-tetrahydroxyxanthone, 1,3,6,8tetrahydroxyxanthone, 1,4,6-trihydroxyxanthone, 1,3,5-trihydroxyxanthone, 1,3,6-trihydroxyxanthone, 1,3,8-trihydroxyxanthone, 1,3-dihydroxyxanthone, and 1,6-diyhdroxyxanthone.

* * * * *

UNITED STATES PATENT AND TRADEMARK OFFICE
CERTIFICATE OF CORRECTION

PATENT NO. : 4,987,150

DATED : January 22, 1991

INVENTOR(S) : Masayasu KURONO et al

It is certified that error appears in the above-identified patent and that said Letters Patent is hereby corrected as shown below:

On the title page, Item [30], "Dec. 5, 1988", should read -- May 12, 1988 --.

Signed and Sealed this

Sixth Day of October, 1992

*Attest:*

DOUGLAS B. COMER

*Attesting Officer*      *Acting Commissioner of Patents and Trademarks*